(12) United States Patent
Xu et al.

(10) Patent No.: US 11,844,502 B2
(45) Date of Patent: Dec. 19, 2023

(54) MULTI-DEGREE-OF-FREEDOM FLEXIBLE SURGICAL INSTRUMENT

(71) Applicant: BEIJING SURGERII ROBOTICS COMPANY LIMITED, Beijing (CN)

(72) Inventors: Kai Xu, Beijing (CN); Zhengchen Dai, Beijing (CN); Tianlai Dong, Beijing (CN); Jiangran Zhao, Beijing (CN); Huan Liu, Beijing (CN); Yuyang Chen, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 1050 days.

(21) Appl. No.: 16/329,234

(22) PCT Filed: Aug. 31, 2017

(86) PCT No.: PCT/CN2017/099852
§ 371 (c)(1),
(2) Date: Feb. 28, 2019

(87) PCT Pub. No.: WO2018/041202
PCT Pub. Date: Mar. 8, 2018

(65) Prior Publication Data
US 2019/0247032 A1    Aug. 15, 2019

(30) Foreign Application Priority Data
Aug. 31, 2016 (CN) .......................... 201610796050.4

(51) Int. Cl.
*A61B 17/00* (2006.01)
*A61B 34/30* (2016.01)
*A61B 17/29* (2006.01)

(52) U.S. Cl.
CPC ........ *A61B 17/00234* (2013.01); *A61B 34/30* (2016.02); *A61B 2017/00314* (2013.01);
(Continued)

(58) Field of Classification Search
CPC ... A61B 17/00234; A61B 17/29; A61B 34/30; A61B 2017/00314; A61B 2017/00323;
(Continued)

(56) References Cited

U.S. PATENT DOCUMENTS

2008/0255421 A1* 10/2008 Hegeman ............. A61B 1/0055
600/139
2010/0286480 A1* 11/2010 Peine ................... A61B 17/062
600/131
(Continued)

FOREIGN PATENT DOCUMENTS

CN    102697564 A    10/2012
CN    103707322 A    4/2014
(Continued)

OTHER PUBLICATIONS

Xu et al., Design of a Hyper-Redundant Continuum Manipulator for Intra-Cavity Tasks, 2014 IEEE International Conference on Robotics and Biomimetics (Robio 2014), IEEE, Dec. 5, 2014, pp. 380-385.

*Primary Examiner* — Brooke Labranche
(74) *Attorney, Agent, or Firm* — SZDC Law PC

(57) ABSTRACT

A multi-degree-of-freedom flexible surgical instrument that includes a flexible continuous body structure (10) and a driving unit (20) is disclosed. The flexible continuous body structure (10) includes a distal structural body (11), a proximal structural body (16) and a middle connecting body (15). The distal structural body (11) includes a first distal structural segment (12) and a second distal structural segment (13). The proximal structural body (16) includes a proximal structural segment. Second segment structural backbones (163) located on the proximal structural segment are securely connected in one-to-one correspondence to or are the same as second segment structural backbones (133) located on the second distal structural segment (13). The
(Continued)

middle connecting body (15) includes channel fixing plates (152), channel fixing blocks (153), first structural backbone guide channels (151) and second structural backbone guide channels (154).

17 Claims, 8 Drawing Sheets

(52) U.S. Cl.
 CPC ............... *A61B 2017/00323* (2013.01); *A61B 2017/2932* (2013.01)

(58) Field of Classification Search
 CPC .. A61B 2017/2932; A61B 2017/00327; A61B 2017/00398; A61B 2017/291; A61B 2017/2943
 See application file for complete search history.

(56) References Cited

U.S. PATENT DOCUMENTS

| | | |
|---|---|---|
| 2013/0090763 A1 | 4/2013 | Simaan et al. |
| 2013/0289478 A1 | 10/2013 | Kim et al. |
| 2015/0313619 A1 | 11/2015 | Tadano et al. |
| 2017/0231703 A1* | 8/2017 | Diel ................. A61B 34/35 74/89.14 |

FOREIGN PATENT DOCUMENTS

| | | |
|---|---|---|
| CN | 103948435 A | 7/2014 |
| CN | 104758060 A | 7/2015 |
| CN | 105751210 A | 7/2016 |
| CN | 106236269 A | 12/2016 |
| EP | 2008594 A2 | 12/2008 |
| WO | 2008144077 A1 | 11/2008 |

* cited by examiner

MULTI-DEGREE-OF-FREEDOM FLEXIBLE SURGICAL INSTRUMENT

CROSS REFERENCE TO RELATED APPLICATIONS

This patent application is the National Stage Application of PCT/CN2017/099852, filed on Aug. 31, 2017, which claims the priority of Chinese patent application No. 201610796050.4 filed on Aug. 31, 2016, entitled "Multi-degree-of-freedom flexible surgical instrument", which is incorporated herein by reference in its entirety.

TECHNICAL FIELD

The present invention relates to a multi-degree-of-freedom flexible surgical instrument, belonging to the field of medical instruments.

BACKGROUND ART

In the modern medical field, the manual multi-port laparoscopic minimally invasive surgery has been widely used in clinical practice. Such minimally invasive surgery has successfully reduced the postoperative pain, complications and hospital stays for rehabilitation of patients and improved the postoperative scar. In order to further reduce the surgical injury and reduce the pain of patients, the researchers have proposed the single-port laparoscopic minimally invasive surgery.

Compared with a multi-port laparoscopic minimally invasive procedure that needs multiple incisions on the body surface, in a single-port laparoscopic minimally invasive procedure, all surgical instruments are inserted into the abdominal cavity via one incision on the body surface (usually via the navel), thereby further reducing the injury to the patient. However, such a single-port configuration has higher demands on both the design of the surgical instruments and the operation of the doctor during the procedure.

Conventional rigid surgical instruments are mostly of an elongated rod-like structure and are provided with a surgical end effector at the end of the instrument to perform motion control by pulling a wire or a rope. Since the manual single-port laparoscopic surgery based on the conventional rigid surgical instruments has the problems of the complicated hand-eye coordination operation requirements, the limited flexibility of the surgical instruments and the small operation range, the manual single-port laparoscopic surgery has not been widely used in clinical practice.

SUMMARY OF THE INVENTION

Aiming at the above problems, an object of the present invention is to provide a multi-degree-of-freedom flexible surgical instrument that can be better applied to operations performed through a surgical incision or multiple surgical incisions.

In order to achieve the above objective, the following technical solutions are used in the invention: a multi-degree-of-freedom flexible surgical instrument, comprising a flexible continuous body structure and a driving unit, wherein the flexible continuous body structure comprises a distal structural body, a proximal structural body and a middle connecting body; the distal structural body comprises a first distal structural segment and a second distal structural segment, the first distal structural segment comprising first distal spacing disks, a first distal fixing disk and first segment structural backbones, and the second distal structural segment comprising second distal spacing disks, a second distal fixing disk and second segment structural backbones; the proximal structural body comprises a proximal structural segment, and the proximal structural segment comprises proximal spacing disks, a proximal fixing disk and second segment structural backbones; the second segment structural backbones located on the proximal structural segment are securely connected in one-to-one correspondence to or are the same as the second segment structural backbones located on the second distal structural segment; the middle connecting body comprises channel fixing plates, channel fixing blocks, first structural backbone guide channels and second structural backbone guide channels, the channel fixing blocks being located between the two channel fixing plates, the first structural backbone guide channels being securely connected between the channel fixing blocks and the channel fixing plate near the distal structural body, and the second structural backbone guide channels being securely connected between the two channel fixing plates; one end of the second segment structural backbone is securely connected to the proximal fixing disk, and the other end of the second segment structural backbone passes through the proximal spacing disks, the second structural backbone guide channel, the first distal structural segment and the second distal spacing disks in sequence and is then securely connected to the second distal fixing disk; and the driving unit comprises a proximal structural segment driving handle and a first distal structural segment driving assembly, the proximal structural segment driving handle being securely connected to the proximal fixing disk, the first distal structural segment driving assembly being located between the two channel fixing plates, and an output end of the first distal structural segment driving assembly comprising two sliders moving in opposite directions along a straight line, and one end of the first segment structural backbone being securely connected to the slider, and the other end of the first segment structural backbone passing through the channel fixing block, the first structural backbone guide channel and the first distal spacing disks in sequence and being then securely connected to the first distal fixing disk.

In one preferred embodiment, the first distal structural segment driving assembly comprises a fixing base, a motor, a pair of gears, a worm, a worm gear, a transmission shaft, a connecting rod, guide rods and the sliders; the fixing base is securely connected to the channel fixing plates, the motor is securely connected to the fixing base, an output shaft of the motor is coaxially and securely connected to one of the gears in the pair of gears, the other gear in the pair of gears is coaxially and securely connected to the worm, the worm meshes with the worm gear, the worm gear is securely sheathed over the transmission shaft, the transmission shaft is rotatably connected to the fixing base, and the transmission shaft is securely connected to the middle of the connecting rod; two sliders are provided, and are respectively located on the left and right sides of the transmission shaft and slidably connected to the guide rods, and the guide rods are securely connected between the two channel fixing plates; and two ends of the connecting rod are respectively connected to one of the sliders.

In one preferred embodiment, a front end of the distal structural body is provided with a surgical end effector, and a actuation wire of the surgical end effector passes through the distal structural body, the middle connecting body and the proximal structural body, and the other end of the actuation wire is connected to a surgical end effector driving mechanism arranged in the proximal structural segment driving handle; the surgical end effector driving mechanism comprises a driving slider, a transmission slider, a connecting spring, a guide rod, a driving rod, a connecting rod and a driving mechanism fixing plate; the driving mechanism fixing plate is securely connected to the proximal structural segment driving handle, and the guide rod is arranged between a rear end of the proximal structural segment driving handle and the driving mechanism fixing plate; the driving slider is slidably connected to the guide rod and is securely connected to the actuation wire; the transmission slider is slidably connected to the guide rod located at a front side of the driving slider, and the transmission slider is connected to the connecting spring by means of the driving slider; and one end of the driving rod is rotatably connected to the proximal structural segment driving handle, and the middle of the driving rod is connected to the transmission slider by means of the connecting rod.

In one preferred embodiment, a actuation wire guide channel is provided between the channel fixing plate near the distal structural body and the driving mechanism fixing plate, and the actuation wire passes through the actuation wire guide channel.

Two ends of the connecting rod are respectively provided with a sliding groove; a cylindrical protrusion is provided at one end of each of the sliders, and the cylindrical protrusion of the slider is limited in the sliding groove of the connecting rod; and the distances from the planes of motion of the two sliders to the center of rotation of the connecting rod are equal.

In one preferred embodiment, the flexible surgical instrument further comprises a flexible surgical instrument housing and a proximal structural segment driving handle outer sleeve; the middle connecting body is located inside the flexible surgical instrument housing, and the two channel fixing plates are both securely connected to the flexible surgical instrument housing; and the proximal structural segment driving handle outer sleeve is securely sheathed outside the proximal structural segment driving handle.

In one preferred embodiment, the flexible surgical instrument further comprises a motor driving system, wherein the motor driving system comprises a motor control plate and a slide switch, and the motor control plate is fixedly connected between the two channel fixing plates and is used to control the rotary motion of the motor; and the slide switch is electrically connected to the motor control plate, and the slide switch is provided with three settings for respectively controlling the motor to rotate forward, to maintain the current position and to rotate backward.

In one preferred embodiment, the flexible surgical instrument further comprises a first envelope arranged outside the distal structural body and a second envelope arranged outside the proximal structural body.

The present invention further provides a multi-degree-of-freedom flexible surgical instrument, comprising a flexible continuous body structure and a driving unit, wherein the flexible continuous body structure comprises a distal structural body, a proximal structural body and a middle connecting body; the distal structural body comprises a first distal structural segment and a second distal structural segment, the first distal structural segment comprising first distal spacing disks, a first distal fixing disk and first segment structural backbones, and the second distal structural segment comprising second distal spacing disks, a second distal fixing disk and second segment structural backbones; the proximal structural body comprises a proximal structural segment, and the proximal structural segment comprises a bellows and a second segment structural backbone; the second segment structural backbones located on the proximal structural segment are securely connected in one-to-one correspondence to or are the same as the second segment structural backbones located on the second distal structural segment; the middle connecting body comprises channel fixing plates, channel fixing blocks, first structural backbone guide channels and second structural backbone guide channels, the channel fixing blocks being located between the two channel fixing plates, the first structural backbone guide channels being securely connected between the channel fixing blocks and the channel fixing plate near the distal structural body, and the second structural backbone guide channels being securely connected between the two channel fixing plates; one end of the second segment structural backbone is securely connected to one end of the bellows, and the other end of the second segment structural backbone passes through the bellows, the second structural backbone guide channel, the first distal structural segment and the second distal spacing disks in sequence and is then securely connected to the second distal fixing disk; the driving unit comprises a proximal structural segment driving handle and a first distal structural segment driving assembly, the proximal structural segment driving handle being securely connected to a rear end of the bellows; the first distal structural segment driving assembly is located between the two channel fixing plates, and an output end of the first distal structural segment driving assembly comprises two sliders moving in opposite directions along a straight line; and one end of the first segment structural backbone is securely connected to the slider, and the other end of the first segment structural backbone passes through the channel fixing block, the first structural backbone guide channel and the first distal spacing disks in sequence and is then securely connected to the first distal fixing disk.

In one preferred embodiment, the first distal structural segment driving assembly comprises a fixing base, a motor, a pair of gears, a worm, a worm gear, a transmission shaft, a connecting rod, guide rods and the sliders; the fixing base is securely connected to the channel fixing plates, the motor is securely connected to the fixing base, an output shaft of the motor is coaxially and securely connected to one of the gears in the pair of gears, the other gear in the pair of gears is coaxially and securely connected to the worm, the worm meshes with the worm gear, the worm gear is securely sheathed over the transmission shaft, the transmission shaft is rotatably connected to the fixing base, and the transmission shaft is securely connected to the middle of the connecting rod; two sliders are provided, and are respectively located on the left and right sides of the transmission shaft and slidably connected to the guide rods, and the guide rods are securely connected between the two channel fixing plates; and two ends of the connecting rod are respectively connected to one of the sliders.

The present invention adopts the above technical solutions, and has the following advantages. 1. In the present invention, a flexible continuous body structure comprising a proximal structural body, a middle connecting body and a distal structural body is used as the main body, wherein the distal structural body is composed of a first distal structural segment and a second distal structural segment having a series relationship, the proximal structural body is composed of a proximal structural segment, the proximal structural segment is linked to the second distal structural segment, the proximal structural segment is also linked to a proximal structural segment driving handle, and the first distal structural segment is linked to the first distal structural segment driving assembly, such that the turning motion of the first distal structural segment in the horizontal plane can be controlled by means of the first distal structural segment driving assembly, and the turning motion of the second distal structural segment in any direction can be controlled by means of the proximal structural segment driving handle. 2. In the present invention, a redundant arrangement of structural backbones (the number of the structural backbones being more than three) is used in the distal structural body, the middle connecting body and the proximal structural body, which can improve the stability and load capacity of the system. 3. In the present invention, since the first distal structural segment and the second distal structural segment are driven by a motor and a proximal structural segment driving handle, respectively, an operator can trigger a slide switch linked to the motor while turning the proximal structural segment driving handle, thereby cooperatively driving the turning of the two structural segments in the distal structural body. 4. In the present invention, the front end of the distal structural body is provided with a surgical end effector, and the actuation wire of the surgical end effector passes through the distal structural body and is connected to a surgical end effector driving mechanism in the proximal structural segment driving handle, such that the surgical end effector driving mechanism can achieve the motion control of the surgical end effector by pushing and pulling the actuation wire.

The present invention can be applied to the multi-port laparoscopic surgery, and can also be applied to the single-port laparoscopic surgery.

DETAILED DESCRIPTION OF EMBODIMENTS

The present invention is described in detail below in conjunction with the accompanying drawings and embodiments.

Figure 1:
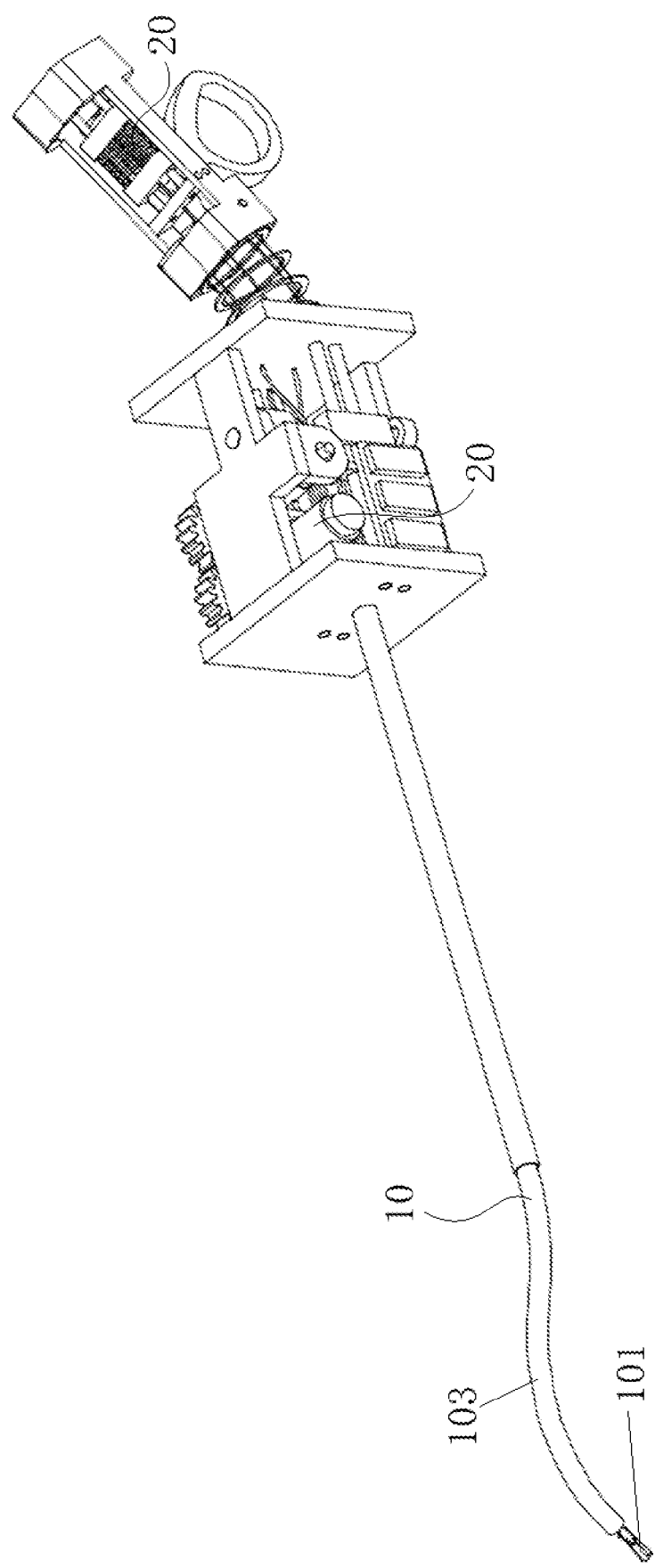
FIG. 1 is an overall structural schematic diagram according to the present invention.

As shown in FIG. 1, the present invention comprises a flexible continuous body structure 10 and a driving unit 20.

Figure 2:
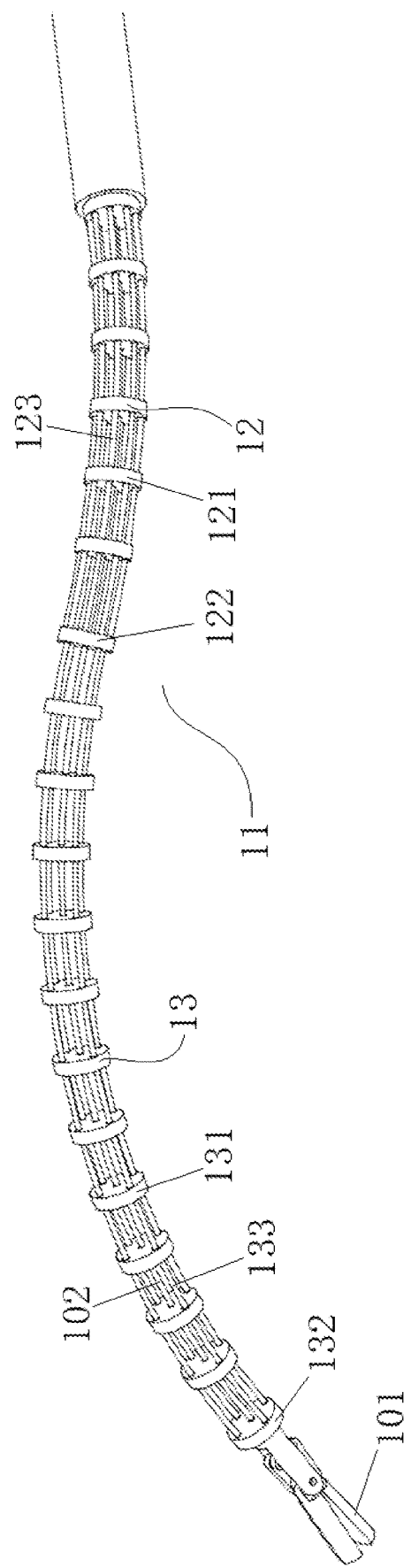
FIG. 2 is a structural schematic diagram of a distal structural body according to the present invention.
Figure 3:
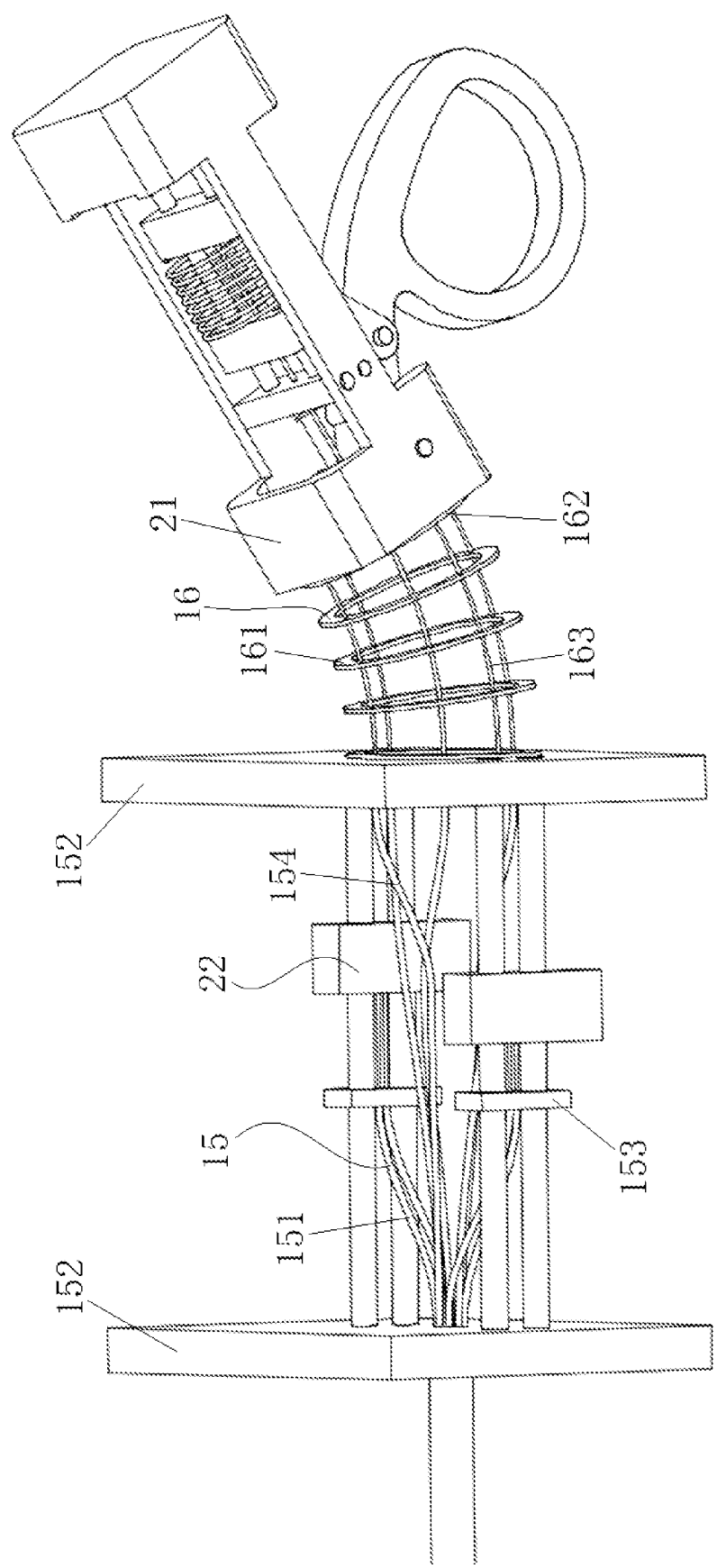
FIG. 3 is a structural schematic diagram according to the present invention with the distal structural body omitted.

The flexible continuous body structure 10 comprises a distal structural body 11 (as shown in FIG. 2), a proximal structural body 16 (as shown in FIG. 3) and a middle connecting body 15. The distal structural body 11 comprises a first distal structural segment 12 and a second distal structural segment 13 having a series connection relationship; and the proximal structural body comprises a proximal structural segment, the proximal structural segment is linked to the second distal structural segment 13 by means of the middle connecting body 15, and when the proximal structural segment turns in any direction, the second distal structural segment 13 correspondingly turns in the opposite direction. The driving unit 20 comprises a proximal structural segment driving handle 21 and a first distal structural segment driving assembly 22, wherein the proximal structural segment driving handle 21 is linked to the proximal structural segment and is used for driving the proximal structural segment to turn in any direction. In addition, the proximal structural segment is also capable of transmitting the overall feed motion and the overall rotary motion from the proximal structural segment driving handle 21 while maintaining the turning shape and length thereof unchanged, thus implementing the overall feed motion and the overall rotary motion of the flexible surgical instrument around its own axis. The first distal structural segment driving assembly 22 is linked to the first distal structural segment 12, and is used for driving the turning motion of the first distal structural segment 12 in a horizontal direction.

As shown in FIG. 2, the first distal structural segment 12 comprises first distal spacing disks 121, a first distal fixing disk 122 and first segment structural backbones 123; and the second distal structural segment 13 comprises second distal spacing disks 131, a second distal fixing disk 132 and second segment structural backbones 132. The first distal spacing disks 121 and the second distal spacing disks 131 are distributed at intervals in the first distal structural segment 12 and the second distal structural segment 13, respectively, and have a function to prevent the first segment structural backbones 123 and the second segment structural backbones 133 from becoming unstable when being pushed.

As shown in FIG. 3, the proximal structural segment comprises proximal spacing disks 161, a proximal fixing disk 162 and second segment structural backbones 163, wherein the proximal spacing disks 161 are distributed at intervals in the proximal structural segment, and have a function to prevent the second segment structural backbones 163 from becoming unstable when being pushed. The second segment structural backbones 163 on the proximal structural segment are securely connected in one-to-one correspondence to or are the same as the second segment structural backbones 133 on the second distal structural segment 13. The number of the first segment structural backbones 123 on the first distal structural segment 12 and the number of the second segment structural backbones 133 on the second distal structural segment 13 are both three or more.

Figure 4:
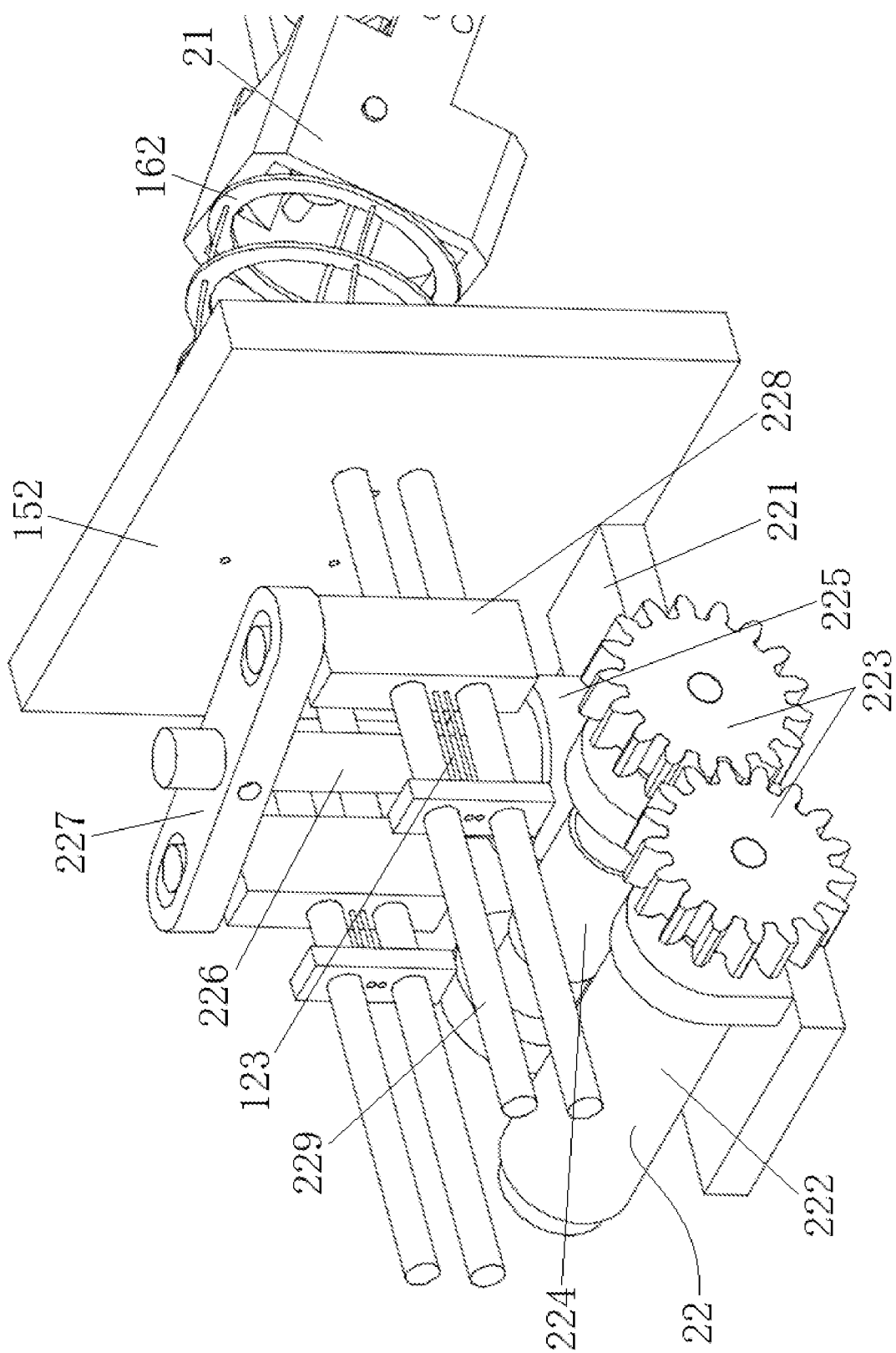
FIG. 4 is a structural schematic diagram of a first distal structural segment driving assembly according to the present invention.

The middle connecting body 15 comprises channel fixing plates 152, channel fixing blocks 153, first structural backbone guide channels 151 and second structural backbone guide channels 154, wherein two channel fixing blocks 153 are arranged at an interval on the left and right and are fixedly connected to guide rods 229 located between the two channel fixing plates 152, the first structural backbone guide channel 151 is securely connected between the channel fixing plate 152 and the channel fixing block 153, and the second structural backbone guide channel 154 is securely connected between the two channel fixing plates 152. One end of the first segment structural backbone 123 is securely connected to an output end slider 228 (as shown in FIG. 4) of the first distal structural segment driving assembly 22, and the other end of the first segment structural backbone passes through the channel fixing block 153, the first structural backbone guide channel 151 and the first distal spacing disks 121 in sequence and is then securely connected to the first distal fixing disk 122. One end of the second segment structural backbone 163 (133) is securely connected to the proximal fixing disk 162, and the other end of the second segment structural backbone passes through the proximal spacing disks 161, the second structural backbone guide channel 154, the first distal structural segment 12 and the second distal spacing disks 131 in sequence and is then securely connected to the second distal fixing disk 132. The first structural backbone guide channel 151 has a function to keep the shape of the first segment structural backbone 123 unchanged under a pushing or pulling force. The second structural backbone guide channel 154 has a function to keep the shape of the second segment structural backbone 163 (133) unchanged under a pushing or pulling force.

As shown in FIGS. 3 and 4, the first distal structural segment driving assembly 22 comprises fixing bases 221, a motor 222, a pair of gears 223, a worm 224, a worm gear 225, a transmission shaft 226, a connecting rod 227, sliders 228 and guide rods 229. Two fixing bases 221 are provided (only one as shown in FIG. 4), are securely connected to the channel fixing plate 152 and are arranged vertically opposite each other. The motor 222 is securely connected to one of the fixing bases 221, an output shaft of the motor 222 is coaxially and securely connected to one of the gears in the pair of gears 223, the other gear in the pair of gears 223 is coaxially and securely connected to the worm 224, the worm 224 meshes with the worm gear 225, the worm gear 225 is securely sheathed over the transmission shaft 226, the transmission shaft 226 is rotatably supported between the two fixing bases 221, and the transmission shaft 226 is securely connected to the middle of the connecting rod 227. Two sliders 228 are provided, are located on the left and right sides of the transmission shaft 226 and are respectively slidably connected to the guide rods 229, and the guide rods 229 are securely connected between the two channel fixing plates 152. Two ends of the connecting rod 227 are respectively connected to one of the sliders 228, and the two sliders 228 serve as an output end of the first distal structural segment driving assembly 22. The rotary power of the motor 222 may be transmitted to the transmission shaft 226 by means of the pair of gears 223, the worm 224 and the worm gear 225, so as to drive the connecting rod 227 to rotate, and the rotation of the connecting rod 227 is converted into a linear motion of the sliders 228 along the guide rods 229, thus forming the cooperative pushing and pulling for the first segment structural backbones 123 to drive the first structural segment 12 to turn in a horizontal direction.

Figure 5:
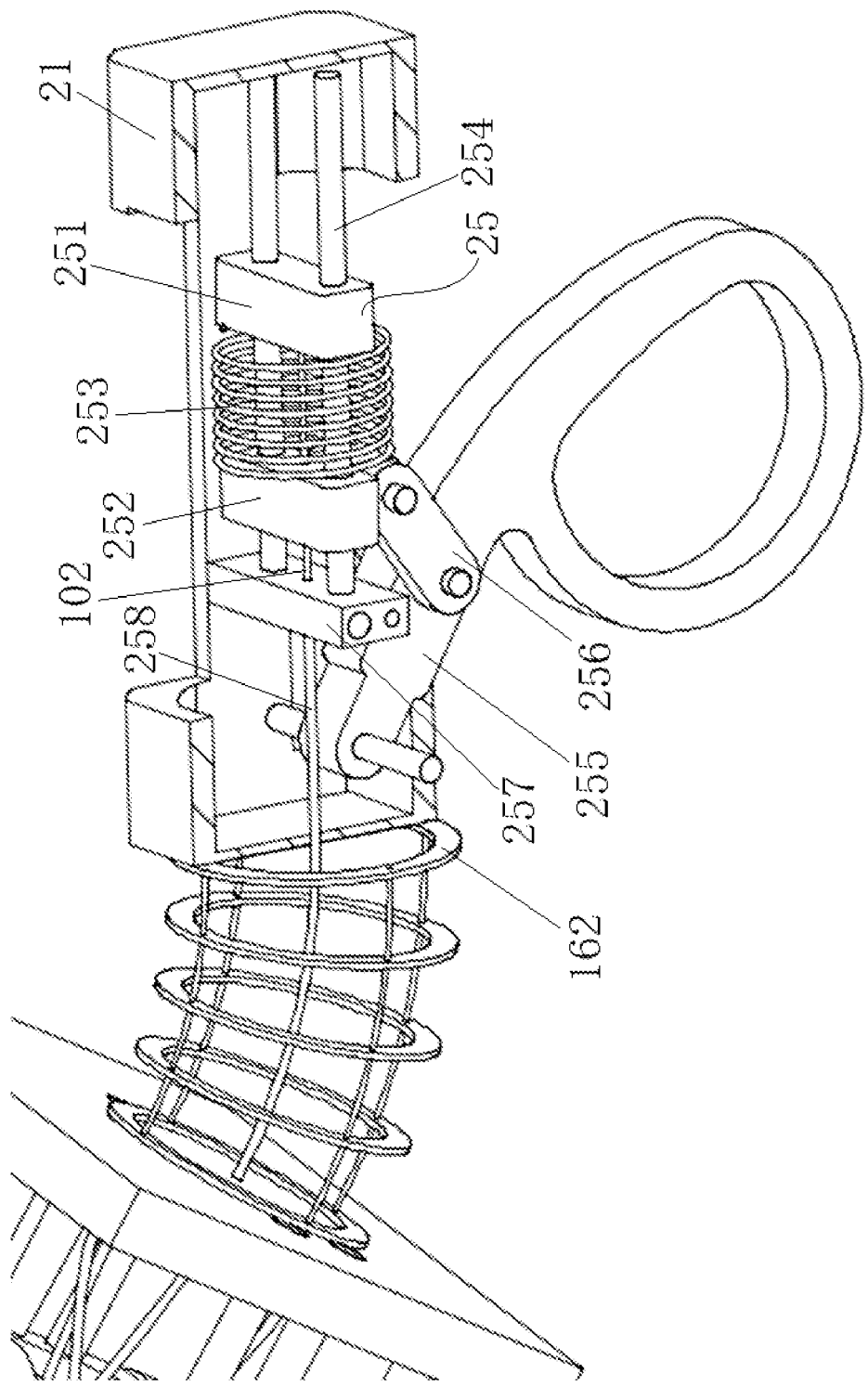
FIG. 5 is a structural schematic diagram of a surgical end effector driving mechanism according to the present invention.

As shown in FIGS. 3 and 5, the proximal structural segment driving handle 21 is securely connected to the proximal fixing disk 162, applying a turning torque to the proximal structural segment driving handle 21 may control the proximal structural body 16 to turn, and the proximal structural body 16 turns in an approximately circular arc shape under the drive of the proximal structural segment driving handle 21.

In the above embodiment, as shown in FIGS. 2 and 5, a front end of the distal structural body 11 is provided with a surgical end effector 101, a actuation wire 102 of the surgical end effector 101 passes through the distal structural body 11, the middle connecting body 15 and the proximal structural body 16, and the other end of the actuation wire is connected to a surgical end effector driving mechanism 25 arranged in the proximal structural segment driving handle 21. The surgical end effector driving mechanism 25 comprises a driving slider 251, a transmission slider 252, a connecting spring 253, a guide rod 254, a driving rod 255, a connecting rod 256 and a driving mechanism fixing plate 257. The driving mechanism fixing plate 257 is securely connected to the proximal structural segment driving handle 21, the guide rod 254 is securely arranged between the rear end of the proximal structural segment driving handle 21 and the driving mechanism fixing plate 257. The driving slider 251 is slidably connected to the guide rod 254, and the driving slider 251 is securely connected to the actuation wire 102; and the transmission slider 252 is slidably connected to the guide rod 254 located at a front side of the driving slider 251, and the transmission slider 252 is connected to the driving slider 251 by means of the connecting spring 253. One end of the driving rod 255 is rotatably connected to the proximal structural segment driving handle 21, and the middle of the driving rod 255 is connected to the transmission slider 252 by means of the connecting rod 256. The rotation of the driving rod 255 can push or pull the transmission slider 252 to slide back and forth along the guide rod 254 so as to drive the driving slider 251 by means of the connecting spring 253 to slide back and forth, thus pushing or pulling the actuation wire 102 to implement the motion control for the surgical end effector 101 (such as surgical forceps). The actuation wire 102 of the surgical end effector 101 may also transfer various forms of energy, such as electrical energy and high-frequency vibrations, to achieve specific surgical functions of the surgical end effector 101.

In the above embodiment, a actuation wire guide channel 258 is provided between the channel fixing plate 152 near the distal structural body 11 and the driving mechanism fixing plate 257, and the actuation wire 102 passes through the actuation wire guide channel 258 and has a function to keep the shape of the actuation wire 102 unchanged under a pushing or pulling force.

In the above embodiment, two ends of the connecting rod 227 are respectively provided with a sliding groove; and a cylindrical protrusion is provided at one end of each of the sliders 228, and the cylindrical protrusion of the slider 228 is limited in the sliding groove of the connecting rod 227. In addition, the distances from the planes of motion of the two sliders 228 to the center of rotation of the connecting rod 227 are equal, and thus the connecting rod 227 can drive the two sliders 228 to slide along the guide rod 229 in opposite directions at the same speed of motion, thus cooperatively pushing and pulling the first segment structural backbones 123.

Figure 6:
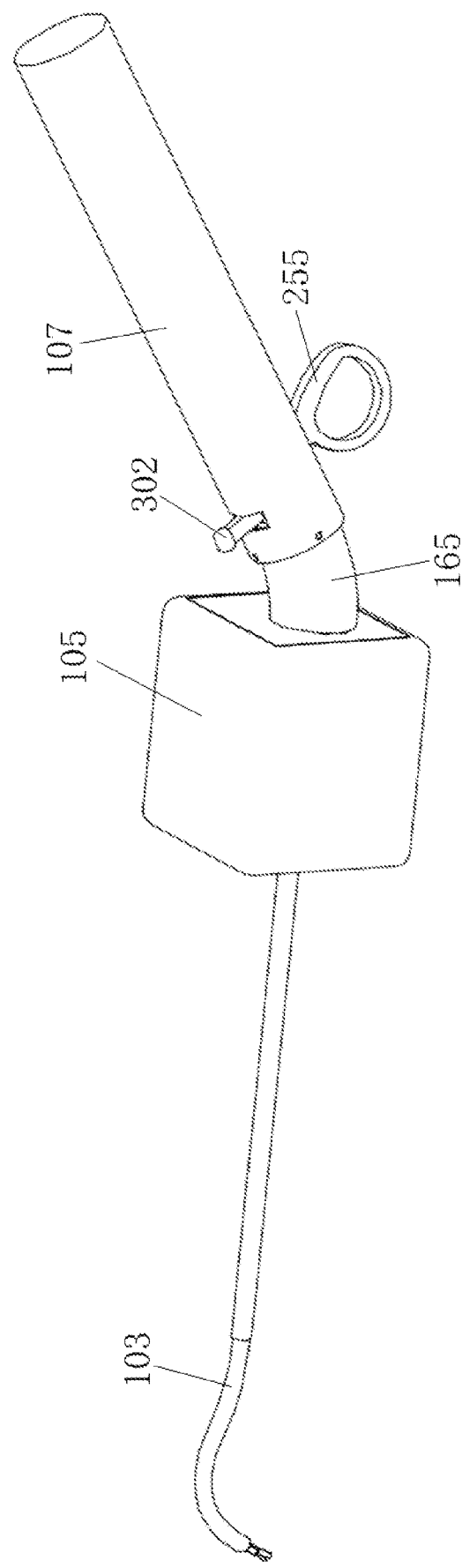
FIG. 6 is a structural schematic diagram according to the present invention with a flexible surgical instrument housing and a proximal structural segment driving handle outer sleeve being installed.

In the above embodiment, as shown in FIG. 6, the present invention further comprises a flexible surgical instrument housing 105 and a proximal structural segment driving handle outer sleeve 107, wherein the middle connecting body 15 is located inside the flexible surgical instrument housing 105, and the two channel fixing plates 152 are both securely connected to the flexible surgical instrument housing 105; and the proximal structural segment driving handle outer sleeve 107 is securely sheathed outside the proximal structural segment driving handle 21. The flexible surgical instrument housing 105 and the proximal structural segment driving handle outer sleeve 107 enclose the driving unit 20 and isolate the driving unit from the outside, such that the present invention can be sterilized as a whole before use to ensure the practicability of clinical operations.

Figure 7:
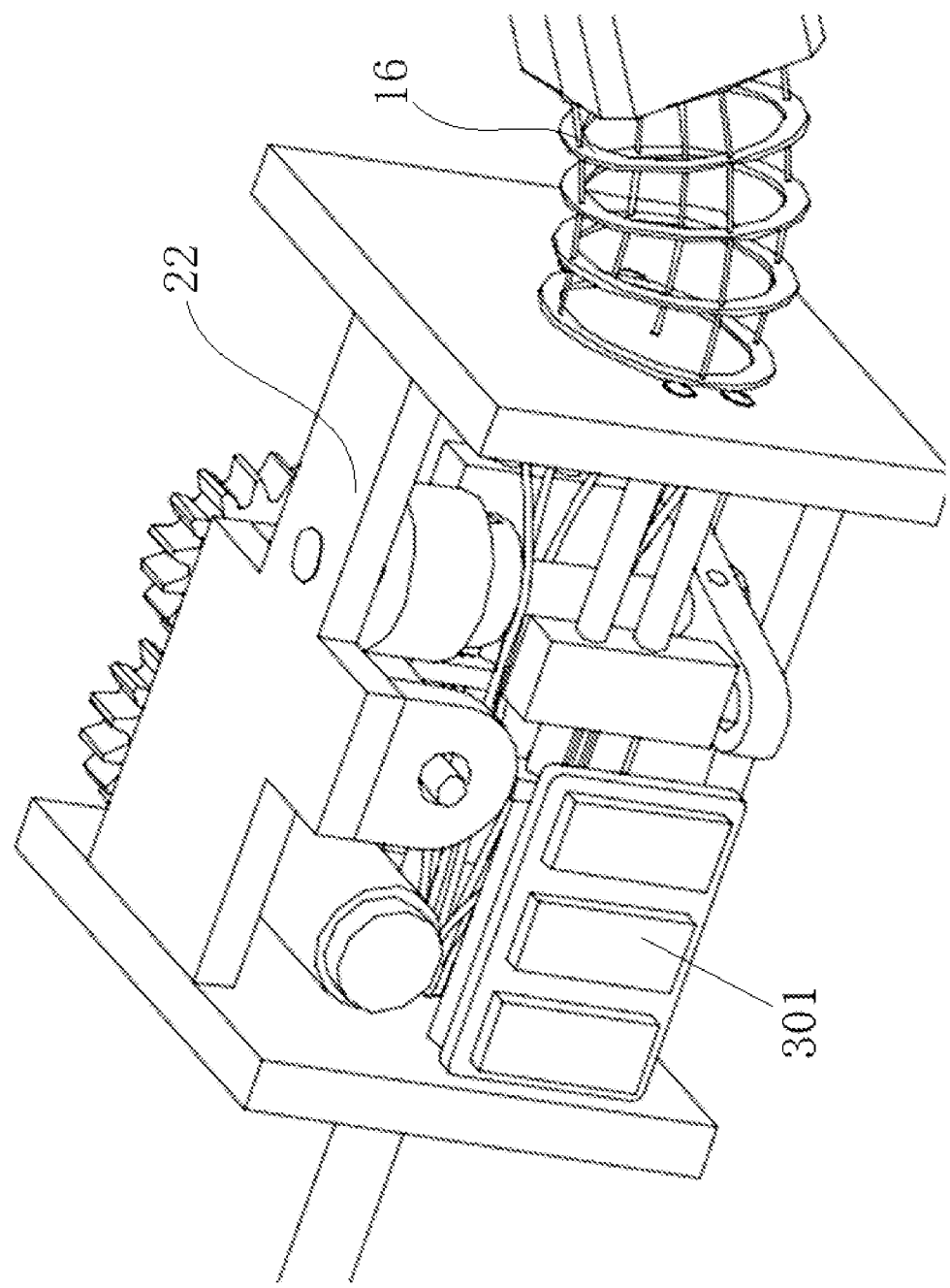
FIG. 7 is a structural schematic diagram of a first distal structural segment driving assembly according to the present invention with a motor control plate being installed.

In the above embodiment, as shown in FIGS. 6 and 7, the present invention further comprises a motor driving system, the motor driving system comprises a motor control plate 301 and a slide switch 302, and the motor control plate 301 is fixedly connected between the two channel fixing plates 152 and is used to control the rotary motion of the motor 222. The slide switch 302 is arranged on the proximal structural segment driving handle outer sleeve 107 and is electrically connected to the motor control plate 301, and the slide switch 302 is provided with three settings for respectively controlling the motor 222 to rotate forward, to maintain the current position and to rotate backward. The slide switch 302 may also be a potentiometer to precisely control the degree of bending of the first distal structural segment 12.

In the above embodiment, as shown in FIG. 1, the present invention further comprises an envelope 103 arranged outside the distal structural body 11 and an envelope 165 arranged outside the proximal structural body 106, and the envelopes 103 and 165 have a function to improve the appearance and also improve the surface smoothness of the distal structural body 11.

Figure 8:
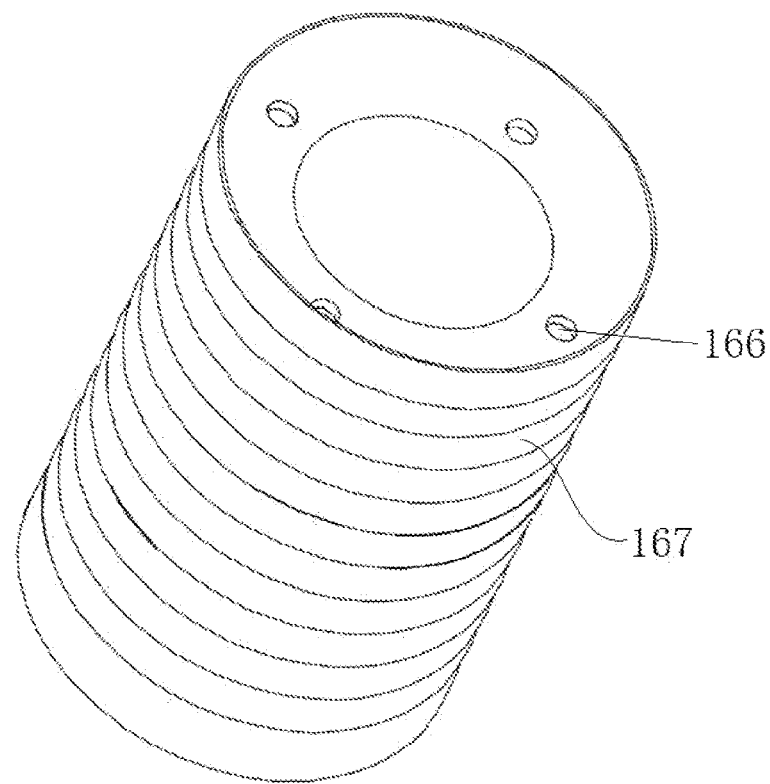
FIG. 8 is a structural schematic diagram of a bellows according to the present invention.
Figure 9:
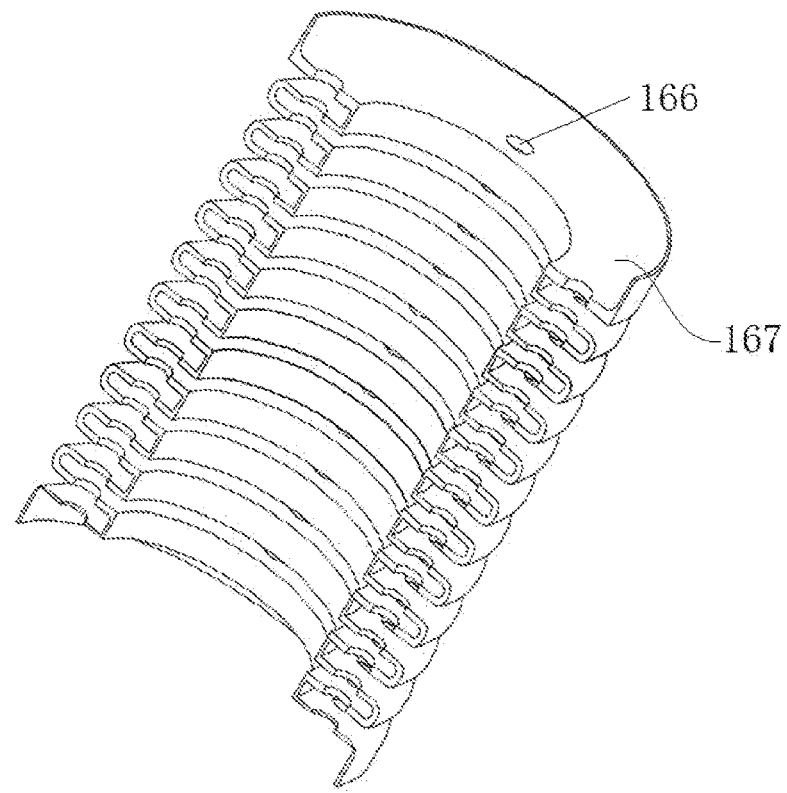
FIG. 9 is structural schematic diagram of a longitudinal section of a bellows according to the present invention.

The proximal structural segment of the present invention proximal structural body 16 may also be of a further structure, and the proximal structural segment in the further structure comprises a bellows 167 (as shown in FIGS. 8 and 9) and second segment structural backbones 163, wherein one end of the second segment structural backbone 163 is securely connected to one end of the bellows 167, and the other end of the second segment structural backbone passes through a through-hole 166 on the bellows 167, the second structural backbone guide channel 154, the first distal structural segment 12 and the second distal spacing disks 131 in sequence and is then securely connected to the second distal fixing disk 132.

The present invention has been illustrated only by the above embodiment, and the structure, arrangement position and connection of the components can be varied. On the basis of the technical solutions of the present invention, the improvements or equivalent changes to individual components according to the principles of the present invention should not be excluded from the scope of protection of the present invention.

The invention claimed is:

1. A flexible surgical instrument, comprising:
a distal structural body comprising at least one distal structural segment, the at least one distal structural segment comprises a first distal structural segment and a second distal structural segment, the first distal structural segment comprises a first distal fixing disk and first distal segment structural backbones, the second distal structural segment comprises a second distal fixing disk and second distal segment structural backbones, distal ends of the first distal segment structural backbones of the first distal structural segment are securely connected to the first distal fixing disk, distal ends of the second distal segment structural backbones of the second distal structural segment are securely connected to the second distal fixing disk, and proximal ends of the second distal segment structural backbones of the second distal structural segment pass through the first distal structural segment;
a proximal structural body comprising at least one proximal structural segment, the at least one proximal structural segment comprising a proximal fixing disk, and proximal segment structural backbones, the proximal segment structural backbones being are securely connected to or the same as corresponding second distal segment structural backbones of the second distal structural segment, proximal ends of the proximal segment structural backbones of the at least one proximal structural segment are securely connected to the proximal fixing disk;
a driving unit comprising a proximal structural segment driving handle securely connected to the at least one proximal structural segment to turn or rotate the at least one proximal structural segment,
wherein the driving unit further comprises a first distal structural segment driving assembly, a pair of first distal segment structural backbones of the first distal structural segment are connected to the first distal structural segment driving assembly,
wherein the first distal structural segment driving assembly is operable to control a turning motion of the first distal structural segment by cooperatively pushing or pulling the pair of first distal segment structural backbones of the first distal structural segment, and
wherein the first distal structural segment driving assembly comprising a first slider and a second slider; the first slider and the second slider are operable to perform linear motion in opposite directions, and the pair of first distal segment structural backbones of the first distal structural segment are connected to the first slider and the second slider, respectively.

2. The flexible surgical instrument of claim 1, wherein the proximal structural segment driving handle is securely connected to the proximal fixing disk.

3. The flexible surgical instrument of claim 1, wherein:
the at least one proximal structural segment further comprises a proximal spacing disk, the proximal segment structural backbone of the at least one proximal structural segment passing through the proximal spacing disk; and
the first distal structural segment further comprises a first distal spacing disk, the first distal segment structural backbone of the first distal structural segment passing through the first distal spacing disk, the second distal structural segment further comprises a second distal spacing disk, the second distal segment structural backbone of the second distal structural segment passing through the second distal spacing disk.

4. The flexible surgical instrument of claim 1, wherein:
the at least one proximal structural segment comprises: a bellows, the proximal segment structural backbone of the at least one proximal structural segment passing through the bellows.

5. The flexible surgical instrument of claim 1, further comprising a middle connecting body comprising:
a first channel fixing plate close to the distal structural body;
a second channel fixing plate close to the proximal structural body;
first structural backbone guide channels disposed between the first channel fixing plate and the second channel fixing plate; and
second structural backbone guide channels disposed between the first channel fixing plate and the second channel fixing plate; wherein:
the first distal segment structural backbones of the first distal structural segment pass through the first structural backbone guide channel;
the second distal segment structural backbones of the second distal structural segment pass through the second structural backbone guide channel.

6. The flexible surgical instrument of claim 5, wherein the first distal structural segment driving assembly is disposed between the two channel fixing plates.

7. The flexible surgical instrument of claim 6, wherein the first distal structural segment driving assembly further comprises:
a fixing base securely connected to the first channel fixing plate or the second channel fixing plate;
a transmission shaft comprising a first end rotatably connected to the fixing base; and
a connecting rod comprising two sliding grooves disposed in two ends of the connecting rod, respectively, and a second end of the transmission shaft being securely connected between the two sliding grooves; the first slider comprising a first protrusion end disposed at one of the two sliding grooves; and the second slider comprising a second protrusion end disposed at the other one of the two sliding grooves.

8. The flexible surgical instrument of claim 7, wherein the first distal structural segment driving assembly further comprises a worm transmission part disposed at the fixing base and configured to rotate the transmission shaft.

9. The flexible surgical instrument of claim 5, further comprising a flexible surgical instrument housing, wherein the middle connecting body is disposed inside the flexible surgical instrument housing.

10. The flexible surgical instrument of claim 1, further comprising:
a surgical end effector disposed at a distal end of the distal structural body; and
a surgical end effector actuation wire passing through the distal structural body, the surgical end effector actuation wire comprising a proximal end securely connected to a surgical end effector driving mechanism and a distal end securely connected to the surgical end effector.

11. The flexible surgical instrument of claim 10, wherein the surgical end effector driving mechanism is arranged in the proximal structural segment driving handle.

12. The flexible surgical instrument of claim 11, wherein the surgical end effector driving mechanism comprises:
a guide rod disposed in the proximal structural segment driving handle;
a driving slider slidably connected to the guide rod, the distal end of the actuation wire being securely connected to the driving slider; and
a driving rod to drive the driving slider.

13. The flexible surgical instrument of claim 12, wherein the surgical end effector driving mechanism further comprises:
a transmission slider slidably connected to the guide rod and disposed at a front side of the driving slider; and
a connecting spring comprising a first end connected to the transmission slider and a second end connected to the driving slider,
the driving rod being rotatably connected to the proximal structural segment driving handle and driving the transmission slider to perform a linear motion.

14. The flexible surgical instrument of claim 10, further comprising an actuation wire guide channel, and the actuation wire passes through the actuation wire guide channel.

15. The flexible surgical instrument of claim 1, further comprising an envelope covering the distal structural body.

16. A flexible surgical instrument system, comprising:
a flexible surgical instrument:
a distal structural body comprising at least one distal structural segment, the at least one distal structural segment including a first distal structural segment and a second distal structural segment, the first distal structural segment comprises a first distal fixing disk and first distal segment structural backbones, the second distal structural segment comprises a second distal fixing disk and second distal segment structural backbones, distal ends of the first distal segment structural backbones of the first distal structural segment are securely connected to the first distal fixing disk, distal ends of the second distal segment structural backbones of the second distal structural segment are securely connected to the second distal fixing disk, and proximal ends of the second distal segment structural backbones of the second distal structural segment pass through the first distal structural segment;
a proximal structural body comprising at least one proximal structural segment, the at least one proximal structural segment comprising a proximal fixing disk, and proximal segment structural backbones, the proximal segment structural backbones are securely connected to or the same as corresponding second distal segment structural backbones of the second distal structural segment, proximal ends of the proximal segment structural backbones of the at least one proximal structural segment are securely connected to the proximal fixing disk;
a driving unit comprising:
a proximal structural segment driving handle securely connected to the at least one proximal structural segment to turn or rotate the at least one proximal structural segment;
a first distal structural segment driving assembly, wherein a pair of first distal segment structural backbones of the first distal structural segment are connected to the first distal structural segment driving assembly, and the first distal structural segment driving assembly is operable to control a turning motion of the first distal structural segment by cooperatively pushing or pulling the pair of first distal segment structural backbones of the first distal structural segment; wherein the first distal structural segment driving assembly comprising a first slider and a second slider; the first slider and the second slider are operable to perform linear motion in opposite directions, and the pair of first distal segment structural backbones of the first distal structural segment are connected to the first slider and the second slider, respectively; and
a motor assembly operable to drive the first distal structural segment driving assembly.

17. The flexible surgical instrument system of claim 16, wherein the motor assembly comprising:
a motor to drive the first distal structural segment driving assembly; and
a motor driving system comprising:
a motor control plate to control a rotary motion of the motor; and
a slide switch electrically connected to the motor control plate.

* * * * *